United States Patent [19]

Cascone

[11] Patent Number: 4,539,176

[45] Date of Patent: Sep. 3, 1985

[54] LOW GOLD DENTAL ALLOYS

[75] Inventor: Paul J. Cascone, Westchester County, N.Y.

[73] Assignee: Pennwalt Corporation, Philadelphia, Pa.

[21] Appl. No.: 607,093

[22] Filed: May 4, 1984

[51] Int. Cl.³ ............................................. C22C 5/04
[52] U.S. Cl. .................................. 420/463; 420/580; 420/589; 433/207
[58] Field of Search .............. 420/463, 464, 465, 580, 420/589; 433/200, 207

[56] References Cited

U.S. PATENT DOCUMENTS

| | | | |
|---|---|---|---|
| 3,134,671 | 5/1964 | Prosen | 420/465 |
| 3,136,634 | 6/1964 | Zwingmann | 420/463 |
| 3,819,366 | 6/1974 | Katz | 420/463 |
| 4,008,080 | 2/1977 | Wagner | 420/589 |
| 4,179,286 | 12/1979 | Knosp | 420/463 |
| 4,400,350 | 8/1983 | Wagner | 420/464 |
| 4,419,325 | 12/1983 | Prasad | 420/464 |

FOREIGN PATENT DOCUMENTS

| | | | |
|---|---|---|---|
| 3146794 | 6/1983 | Fed. Rep. of Germany | 420/463 |
| 3204743 | 8/1983 | Fed. Rep. of Germany | 420/463 |
| 0107436 | 6/1983 | Japan | 420/463 |
| 2048939 | 12/1980 | United Kingdom | 420/463 |

*Primary Examiner*—Peter K. Skiff
*Assistant Examiner*—Robert L. McDowell

[57] ABSTRACT

A silverless low gold dental alloy contains, by weight, 10–40% gold; 3–8% gallium; 0.5–10% indium and/or tin; 0.1 to 1.5% ruthenium, or iridium, or rhenium; balance palladium. The alloy is non-staining and bondable to and compatible with porcelain.

22 Claims, No Drawings

LOW GOLD DENTAL ALLOYS

STATEMENT OF THE INVENTION

The present invention relates to a silverless non-staining, low gold alloy for use in preparing dental prostheses by porcelain fused to metal techniques.

BACKGROUND OF THE INVENTION

In U.S. Pat. No. 4,123,262, I disclose silverless gold base alloys which do not discolor porcelain. The presence of silver in a dental gold alloy used for preparing baked-on porcelain to gold dental restorations often produces staining of the porcelain at the juncture of the porcelain and alloy. The silverless alloys of the present invention are similar in working characteristics to the alloys disclosed in U.S. Pat. No. 4,123,262, but are less costly due to a significant reduction in alloy gold content. The gold content however, is still present in the present alloys in sufficient quantities such that the alloys require no special manufacturing procedures or equipment for their fabrication.

No transition metals (e.g., iron, cobalt, nickel, copper) are included in the present alloys to produce a dark oxide upon heating, thereby reducing processing time since a dark oxide requires removal prior to application of porcelain to the restoration device. The absence of dark oxide formation in my alloys maintains the shade fidelity of the porcelain since the alloy substrate is not continually darkening during porcelain firing.

SUMMARY OF THE INVENTION

Briefly, a variety of useful dental alloys suitable for the porcelain fused to metal technique can be fabricated from alloys containing, by weight:

10 to 40% gold
3 to 8% gallium
0.5 to 10% indium and/or tin
0.1 to 1.5% ruthenium, or iridium, or rhenium balance palladium Preferably, the alloys contain, by weight:

15 to 35% gold
4.5 to 6.5% gallium
2 to 6% tin
0.1 to 0.8% ruthenium balance palladium

DETAILED DESCRIPTION OF THE INVENTION

Many of the dental alloys of the present invention are exemplified in the table below. Fabrication of these alloys may be simplified through the use of binary components such, for example, as 96Pd-4Ru, 65Pd-35Ga, 70Au-30Ga, and the like.

TABLE

| Element | Examples |  |  |  |  |  |  |  |  |  |  |  |
|---|---|---|---|---|---|---|---|---|---|---|---|---|
| | No. 1 | No. 2 | No. 3 | No. 4 | No. 5 | No. 6 | No. 7 | No. 8 | No. 9 | No. 10 | No. 11 | No. 12 |
| Gold, wt. % | 35 | 35 | 29.5 | 25 | 22.1 | 20 | 17.9 | 17.6 | 15.5 | 11 | 27.7 | 16.9 |
| Gallium, wt. % | 5 | 5 | 4.7 | 6 | 4.8 | 4 | 3.6 | 6.2 | 6 | 7.8 | 2.3 | 4.6 |
| Tin, wt. % | 2.8 | 0 | 0 | 2 | 4.1 | 0 | 6.1 | 0 | 4 | 1.6 | 3.9 | 4.0 |
| Indium, wt. % | 0 | 3 | 2 | 2 | 0 | 10 | 4 | 5.1 | 2 | 0 | 0 | 6.1 |
| Ruthenium, wt. % | 0.6 | 0.6 | 0.1 | 0.12 | 0.1 | 0.8 | 0.1 | 0.1 | 0.1 | 0.12 | 0.1 | 0.1 |
| Palladium balance | | | | | | | | | | | | |
| Yield strength, psi (× 1000) (at 0.2% offset) | 81 | 78 | 68 | 75 | 64 | 73 | 62 | 75 | 75 | 77 | 43 | 124 |
| Elongation, % (in 1") | 8 | 28 | 25 | 10 | 30 | 41 | 36 | 23 | 33 | 18 | 26 | 2 |
| Linear thermal expansion, %, in range from 20° C. to 600° C., measured at 10° C. min | .808 | .799 | .808 | .809 | .800 | .823 | .800 | .812 | .812 | .828 | .784 | .807 |

With the exception of the alloy of Example No. 11, where the gallium content is low, each of the exemplified alloys has a yield strength of at least 60,000 psi, considered adequate for resisting deformation. The alloy of Example No. 11 exhibits a linear thermal expansion of only 0.784%. Linear thermal expansion should be at least 0.79% to insure good porcelain-metal compatability.

Additions of gallium, tin and/or indium increase the thermal expansion coefficient and yield strength of the alloy. Gallium must be present. With regard to expansion and yield strength, gallium is more effective than tin which is more effective than indium. Excessive amounts of gallium, tin and indium produce a brittle alloy having insufficient ductility and elasticity. More specifically, the sum of gallium, tin and indium should comprise at least 6 weight percent of the alloy but no more than about 15 weight percent of gallium and indium; or no more than about 12 weight percent of either gallium and tin, or gallium, tin and indium. Thus, the alloy of Example No. 12 contains 14.6 weight percent of gallium, tin and indium, an excessive amount, which produces a brittle alloy having an elongation of only 2%. A minimum elongation of at least 5% is required, which requirement is satisfied by each of the other alloys of the Examples.

Tin will harden the exemplified alloys faster than indium; therefore, less tin than indium can be accommodated at a given gold content of the alloy before alloy brittleness results. The alloy becomes brittle at a combined weight percent of gallium and tin below 15.

The content of tin should be greater than the content of indium when each is used in order to inhibit formation of a dark oxide. Tin or indium must be present.

The content of gold in the alloys, within the limits specified, is governed by economics.

Generally, as the amount or content of gold is decreased from its upper limit of 40 weight percent to 10 weight percent, or from 35 to 15 weight percent in the preferred alloys, the percentage of base elements (gallium, tin, indium) and ruthenium is increased.

Each of the physical properties of the alloys tabulated above was determined or obtained after a simulated porcelain firing at 1000° C.

Ruthenium, iridium, and rhenium function as grain refiners for the alloys to prevent "hot tearing" which results from stresses produced as the molten metal solidifies in the casting or "investment" mold. The hot alloy has a normal tendency to shrink upon solidification and cooling but is prevented from doing so by the investment mold which is expanding as heat is absorbed by it from the metal therein resulting in tearing of the solidified alloy along grain boundaries. The preferred alloys employ ruthenium as the grain refining agent.

Palladium is a noble metal which imparts basic inertness to the alloys to help resist the environment of the patient's mouth. It is relatively inexpensive, resists oxidation, and possesses good fusion characteristics.

Indium and tin added to the alloys also reduce the melting point thereof, strengthen them, improve their elongation, and form small amounts of adherent oxide on the surfaces of the cast alloy which reacts with the porcelain to produce a chemical bond therebetween. Gallium, like tin and indium, also lowers the melting point of the alloys such that their liquidus temperature (preferably below about 1400° C.) and solidus temperature (preferably above about 1040° C.) are suitable with the porcelain fused to metal technique.

Detailed instructions for making baked-on porcelain to gold dental alloy devices or restorations are given in U.S. Pat. No. 3,981,723, issued to J. J. Tucillo, which patent is assigned to the assignee hereof.

I claim:

1. A low gold dental alloy consisting essentially of, by weight, about 10–40% gold; about 3–8% gallium; about 0.5–10% of at least one element selected from the group consisting of indium and tin; and about 0.1–1.5% of an element selected from the group consisting of ruthenium, iridium, and rhenium; balance palladium.

2. A low gold dental alloy consisting essentially of, by weight,
   about 15 to 35% gold,
   about 4.5 to 6.5% gallium,
   about 2 to 6% tin,
   about 0.1 to 0.8% ruthenium,
   and balance palladium.

3. Alloy of claim 2 comprising, by weight, 35% gold, 5% gallium, 2.8% tin, 0.6% ruthenium, balance palladium.

4. Alloy of claim 1 comprising, by weight, 35% gold, 5% gallium, 3% indium, 0.6% ruthenium, balance palladium.

5. Alloy of claim 1 comprising, by weight, 29.5% gold, 4.7% gallium, 2% indium, 0.1% ruthenium, balance palladium.

6. Alloy of claim 1 comprising, by weight, 25% gold, 6% gallium, 2% tin, 2% indium, 0.12% ruthenium, balance palladium.

7. Alloy of claim 3 comprising, by weight, 22.1% gold, 4.8% gallium, 4.1% tin, 0.1% ruthenium, balance palladium.

8. Alloy of claim 1 comprising, by weight, 20% gold, 4% gallium, 10% indium, 0.8% ruthenium, balance palladium.

9. Alloy of claim 1 comprising, by weight, 17.9% gold, 3.6% gallium, 6.1% tin, 4% indium, 0.1% ruthenium, balance palladium.

10. Alloy of claim 1 comprising, by weight, 17.6% gold, 6.2% gallium, 5.1% indium, 0.1% ruthenium, balance palladium.

11. Alloy of claim 1 comprising, by weight, 15.5% gold, 6% gallium, 4% tin, 2% indium, 0.1% ruthenium, balance palladium.

12. Alloy of claim 1 comprising, by weight, 11% gold, 7.8% gallium, 1.6% tin, 0.12% ruthenium, balance palladium.

13. Alloy of claim 3 having a yield strength of 81,000 psi, an elongation in 1" of 8%, and a linear thermal expansion at 600° C. of 0.808%.

14. Alloy of claim 4 having a yield strength of 78,000 psi, an elongation in 1" of 28%, and a linear thermal expansion at 600° C. of 0.799%.

15. Alloy of claim 5 having a yield strength of 68,000 psi, an elongation in 1" of 25%, and a linear thermal expansion at 600° C. of 0.808%.

16. Alloy of claim 6 having a yield strength of 75,000 psi, an elongation in 1" of 10%, and a linear thermal expansion at 600° C. of 0.809%.

17. Alloy of claim 7 having a yield strength of 64,000 psi, an elongation in 1" of 30%, and a linear thermal expansion at 600° C. of 0.800%.

18. Alloy of claim 8 having a yield strength of 73,000 psi, an elongation in 1" of 41%, and a linear thermal expansion at 600° C. of 0.823%.

19. Alloy of claim 9 having a yield strength of 62,000 psi, an elongation in 1" of 36%, and a linear thermal expansion at 600° C. of 0.800%.

20. Alloy of claim 10 having a yield strength of 75,000 psi, an elongation in 1" of 23%, and a linear thermal expansion at 600° C. of 0.812%.

21. Alloy of claim 11 having a yield strength of 75,000 psi, an elongation in 1" of 33%, and a linear thermal expansion at 600° C. of 0.812%.

22. Alloy of claim 12 having a yield strength of 77,000 psi, an elongation in 1" of 18% and a linear thermal expansion at 600° C. of 0.828%.

* * * * *